US005464819A

United States Patent [19]

Suzuki

[11] Patent Number: 5,464,819

[45] Date of Patent: Nov. 7, 1995

[54] PHYSIOLOGICALLY ACTIVE PEPTIDE HAVING IMMUNOREGULATORY ACTIVITIES

[75] Inventor: Naoyoshi Suzuki, Tokyo, Japan

[73] Assignee: Ajinomoto Co., Inc., Tokyo, Japan

[21] Appl. No.: 729,353

[22] Filed: Jul. 12, 1991

[30] Foreign Application Priority Data

Jul. 12, 1990 [JP] Japan .................................. 2-182714

[51] Int. Cl.$^6$ ............................ A61K 38/00; C07K 5/00; C07K 7/00; C07K 17/00

[52] U.S. Cl. ................................ 514/16; 514/17; 514/18; 514/19; 530/329; 530/330; 530/331

[58] Field of Search ................................ 514/16, 17, 18, 514/19; 530/329, 330, 331

[56] References Cited

U.S. PATENT DOCUMENTS

| | | | |
|---|---|---|---|
| 4,482,543 | 11/1984 | Suzuki et al. | 424/177 |
| 4,897,463 | 1/1990 | Suzuki et al. | 530/329 |
| 5,066,783 | 11/1991 | Cohen et al. | 530/328 |

FOREIGN PATENT DOCUMENTS 0324270 7/1989 European Pat. Off. .

OTHER PUBLICATIONS

Baud et al., Neuroscience Letters, vol. 70 pp. 228–233 (1986).

Kast et al. Cell vol. 59 pp. 603–614 (1989).

Chemical Abstracts 101:5368q (1984).

Chemical Abstracts 101:5369r (1984).

Chemical Abstracts 102:130167v (1985).

Sethi et al., Journal of Immunology, 115, 1151–1158 (1975).

Shirahata et al., Z. Parasitenk. 49, 11–23 (1976).

Nagasawa et al., Immunohiol. 156, 307–319 (1980).

Matsumoto et al., Zbl. Bakt. Hyg., A 250, 383–391 (1981).

Suzuki et al., Zbl. Bakt. Hyg. A 256, 356–366 (1984).

Suzuki et al., Zbl. Bakt. Hyg. A 256, 367–380 (1984).

*Primary Examiner*—Jill Warden
*Assistant Examiner*—Sheela J. Huff
*Attorney, Agent, or Firm*—Birch, Stewart, Kolasch & Birch

[57] ABSTRACT

A novel, substantially pure, physiologically active peptide is disclosed, comprising an amino acid sequence selected from Gly-Glu (SEQ ID NO. 5), Pro-Val-Val (SEQ ID NO. 6), Glu-Pro-Val-Val (SEQ ID NO. 7), Glu-Glu-Pro-Val-Val (SEQ ID NO. 8), Ala-Glu-Glu-Pro-Val-Val (SEQ ID NO. 9), and Gly-Ala-Glu-Glu-Pro-Val-Val (SEQ ID NO. 10). This peptide has immunoregulatory activities, including the activity to inhibit multiplication of *Toxoplasma gondii* inside cells, antibacterial activity, antiviral activity and antitumor activity. A composition comprising at least two peptides selected from the above peptides or comprising at least one peptide selected from the above peptides and at least one additional peptide comprising an amino acid sequence selected from Gly-Glu-Glu-Glu-Glu-Glu (SEQ ID NO. 1), Glu-Glu-Glu-Glu-Glu (SEQ ID NO. 2), Asp-Asp-Asp-Asp-Asp (SEQ ID NO. 3) and Ala-Glu-Glu-Glu-Glu-Glu (SEQ ID NO. 4) is especially useful as an active component for antiprotozoan, antibacterial, antiviral or antitumor agent.

3 Claims, 3 Drawing Sheets

PHYSIOLOGICALLY ACTIVE PEPTIDE HAVING IMMUNOREGULATORY ACTIVITIES

BACKGROUND OF THE INVENTION

1. Field of the Invention

The present invention relates to a novel physiologically active peptide having immunoregulatory activities. More particularly, the present invention is concerned with a novel, substantially pure, physiologically active peptide having immunoregulatory activities, including the activity to inhibit multiplication of Toxoplasma (*Toxoplasma gondii*) inside cells, antibacterial activity, antiviral activity and antitumor activity, and a peptide composition comprising such a novel, substantially pure, physiologically active peptide. Also, the present invention is concerned with a pharmaceutical composition containing this substantially pure, physiologically active peptide as an active component, which composition is useful as an antiprotozoan, antibacterial, antiviral or antitumor agent.

In the present specification, amino acid residues are represented using abbreviations, as indicated below, approved by IUPAC-IUB Commission on Biochemical Nomenclature (CBN). With respect to amino acids and the like having isomers, those represented by the following abbreviations are of the L-configuration unless otherwise specified.

Gln: glutamine residue
Asp: aspartic acid residue
Pro: proline residue
Tyr: tyrosine residue
Val: valine residue
Lys: lysine residue
Glu: glutamic acid residue
Ala: alanine residue
Asn: asparagine residue
Leu: leucine residue
Phe: phenylalanine residue
Gly: glycine residue
His: histidine residue
Ser: serine residue
Thr: threonine residue
Ile: isoleucine residue
Trp: tryptophan residue
Arg: arginine residue
Met: methionine residue
Cys: cysteine residue 2. Discussion of Related Art Toxoplasma is a protozoan parasite which multiplies cheifly in mammalian endothelial cells, and Toxoplasma is feared because it is not only a pathogenic protozoan causing domestic animals to suffer from various diseases but also is a pathogen of human encephalomyelitis. Toxoplasma evades the killing action of a macrophage and, different from other microorganisms, repeats multiplication by binary fission due to endogeneous budding in a macrophage of a normal host.

In Toxoplasma-hyperimmune animals, it has been observed that the macrophages have the activity to kill and digest protozoa. It has been reported that the sera of such Toxoplasma-hyperimmune animals contain a humoral mediator (generally known as "cytokine") capable of inhibiting multiplication of Toxoplasma in the normal cells of the animals (see Sethi, K. K. et al., J. Immunol., vol. 131, pages 1151–1558, 1975).

It has also been reported that a cytokine capable of inhibiting multiplication of Toxoplasma in normal cells is present in the supernatant of a culture obtained by cultivating spleen cells excised from a Toxoplasma-hyperimmune animal in the presence of Toxoplasma lysate antigen (hereinafter referred to as "TLA") (see Shirahata, T., Shimizu, K., and Suzuki, N., Z. Parasitenkd, vol. 49, pages 11–23, 1976).

The above-mentioned cytokine is a glycoprotein having a molecular weight of from 30,000 to 40,000 which is believed to be a substance produced by sensitized T lymphocytes, and it is generally known as "Toxoplasma growth inhibitory factor" (hereinafter referred to simply as "Toxo-GIF") (see Shirahata, T., Shimizu, K., and Suzuki, N., Z. Parasitenkd, vol. 49, pages 11–23, 1976, and Nagasawa, H., et al., Immunobiol., vol. 156, pages 307–319, 1980). This Toxo-GIF inhibits multiplication of Toxoplasma not only in macrophages but also in other somatic cells. In this connection, it should be noted that Toxo-GIF only inhibits multiplication of Toxoplasma in the cells of the same animal species as the host and cannot inhibit multiplication of Toxoplasma in the cells of different animal species (see Nagasawa, H., et al, Immunobiol., vol. 156, pages 307–319, 1980 and Matsumoto, Y., et al., Zbl. Bakt. Hyg., vol. A 250, pages 383–391, 1981). Due to this species specificity, Toxo-GIF cannot be used for the prevention or curing of toxoplasmosis in human beings or various animals other than the host.

In these situations, the present inventor previously found that a low molecular weight substance obtained by hydrolysis of serum from a Toxoplasma-immune animal exhibits not only the species specificity-free activity to inhibit multiplication of Toxoplasma but also antimicroorganism activities against protozoa, bacteria and viruses as well as antitumor activities (see Japanese Patent Application Laid-Open Specification Nos. 57-142922/1982 and 57-144983/1982 and U.S. Pat. No. 4,482,543). The hydrolysate obtained from serum of a Toxoplasma-immune animal has been designated as "Obioactin" (see Suzuki, N., et al., Zbl. Bakt. Hyg. I. Abt. Orig., vol. A 256, pages 356–366, 1984). This Obioactin is a polypeptide substance having a molecular weight of not greater than 5000, and can inhibit multiplication of Toxoplasma not only in homologous cells but also in heterologous cells (see Suzuki, N., et al., Zbl. Bakt. Hyg. I. Abt. Orig., vol. A256, pages 367–380, 1984).

This native Obioactin is believed to be an aggregate or a mixture of a large number of various types of peptides. If it were possible to synthesize Obioactin by identifying active sites for each peptide, the usefulness of Obioactin would markedly increase. However, since Obioactin is believed to be an aggregate or a mixture of a large number of various types of peptides as mentioned above, it is extremely difficult to determine the amino acid sequence for each of the large number of various types of peptides constituting the aggregate or mixture by performing amino acid analysis of purified Obioactin fractions as obtained by chromatographic operations, thereby causing the synthesis of Obioactin to be unfeasible.

The present inventor also previously attempted amino acid analyses for a peptide contained in a fraction of Obioactin purified by reverse phase chromatography in which use was made of ODS-120T column (as described later). A plurality of amino acids were detected for each of the 1st position, the 2nd position, the 3rd position and so forth, as counted from the N-terminus, of the peptide contained in the fraction and, hence, it was impossible to directly determine an amino acid sequence for the peptide from the detected amino acids. However, in such attempts, it was surprisingly found that certain specific amino acid sequences exhibit desired activities (see U.S. Pat. No. 4,897, 463). Accordingly, the specification of U.S. Pat. No. 4,897, 463 discloses a substantially pure peptide comprising an amino acid sequence represented by a formula selected from the group consisting of formulae (7) to (10):

Gly-Glu-Glu-Glu-Glu-Glu (7), (SEQ ID NO. 1)

Glu-Glu-Glu-Glu-Glu (8), (SEQ ID NO. 2)

Asp-Asp-Asp-Asp-Asp (9), (SEQ ID NO. 3)

and

Ala-Glu-Glu-Glu-Glu-Glu (10), (SEQ ID NO. 4).

Among these peptides having the amino acid sequences represented by the above formulae (7) to (10), the peptide having the amino acid sequence represented by formula (7) exhibits the highest activity to inhibit multiplication of Toxoplasma inside cells. This peptide having the amino acid sequence represented by formula (7) has been designated by the present inventor as Obiopeptide-1 (hereinafter referred to simply as "Obio-1").

SUMMARY OF THE INVENTION

On the assumption that there should be other peptides which form active sites in peptides among a large number of various types of peptides constituting Obioactin and which have amino acid sequences other than those represented by the above formulae (7) to (10), the present inventor has made further extensive and intensive studies to develop novel and useful peptides by confirming the existence, determining the structure and evaluating the activity of such other peptides. As a result, the present inventor has succeeded in isolating six novel peptides, which are believed to individually constitute the above-mentioned active sites, and has confirmed their immunoregulatory activities including the activity to inhibit multiplication of Toxoplasma, antibacterial activity, antitumor activity and antiviral activity. Further, unexpectedly, the present inventor has found that a peptide composition comprising at least two peptides selected from these six novel peptides and a peptide composition comprising at least one peptide selected from these six novel peptides and at least one aditional peptide selected from those having the amino acid sequences represented by the above formulae (7) to (10) surprisingly exert a synergistic effect. Based on these findings, the present invention has been completed.

Accordingly, it is an object of the present invention to provide a novel physiologically active peptide having immunoregulatory activities including the activity to inhibit multiplication of Toxoplasma, antibacterial activity, antitumor activity and antiviral activity.

It is another object of the present invention to provide a novel physiologically active peptide composition having improved immunoregulatory activities.

It is a further object of the present invention to provide a pharmaceutical composition useful as antiprotozoan, antibacterial, antiviral or antitumor agent.

The foregoing and other objects, features and advantages of the present invention will be apparent from the following detailed description and appended claims taken in connection with the accompanying drawings.

DETAILED DESCRIPTION OF THE INVENTION

Figure 1:
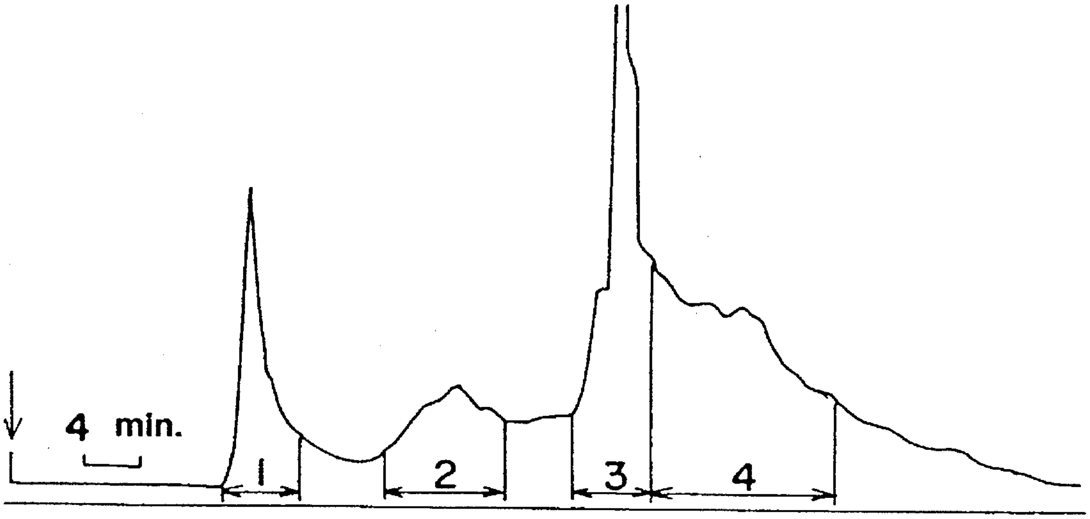
FIG. 1 shows a chromatogram obtained by high performance liquid chromatography of crude Obioactin, which chromatogram indicates four fractions.

In one aspect of the present invention, there is provided a substantially pure, physiologically active peptide comprising an amino acid sequence represented by a formula selected from the group consisting of formulae (1) to (6):

Gly-Glu (1), (SEQ ID NO. 5)

Pro-Val-Val (2), (SEQ ID NO. 6)

Glu-Pro-Val-Val (3), (SEQ ID NO. 7)

Glu-Glu-Pro-Val-Val (4), (SEQ ID NO. 8)

Ala-Glu-Glu-Pro-Val-Val (5), (SEQ ID NO. 9)

and

Gly-Ala-Glu-Glu-Pro-Val-Val (6), (SEQ ID NO. 10).

In another aspect of the present invention, there is provided a physiologically active peptide composition comprising at least two peptides selected from the group consisting of substantially pure, physiologically active peptides respectively comprising amino acid sequences of formulae (1) to (6):

Gly-Glu (1), (SEQ ID NO. 5)

Pro-Val-Val (2), (SEQ ID NO. 6)

Glu-Pro-Val-Val (3), (SEQ ID NO. 7)

Glu-Glu-Pro-Val-Val (4), (SEQ ID NO. 8)

Ala-Glu-Glu-Pro-Val-Val (5), (SEQ ID NO. 9)

and

Gly-Ala-Glu-Glu-Pro-Val-Val (6), (SEQ ID NO. 10).

In a further aspect of the present invention, there is provided a physiologically active peptide composition comprising at least one peptide selected from the group consisting of substantially pure, physiologically active peptides respectively comprising amino acid sequences of formulae (1) to (6):

Gly-Glu (1), (SEQ ID NO. 5)

Pro-Val-Val (2), (SEQ ID NO. 6)

Glu-Pro-Val-Val (3), (SEQ ID NO. 7)

Glu-Glu-Pro-Val-Val (4), (SEQ ID NO. 8)

Ala-Glu-Glu-Pro-Val-Val (5), (SEQ ID NO. 9)

and

Gly-Ala-Glu-Glu-Pro-Val-Val (6); (SEQ ID NO. 10)

and at least one peptide selected from the group consisting of substantially pure, physiologically active peptides respectively comprising amino acid sequences of formulae (7) to (10):

Gly-Glu-Glu-Glu-Glu-Glu (7), (SEQ ID NO. 1)

Glu-Glu-Glu-Glu-Glu (8), (SEQ ID NO. 2)

Asp-Asp-Asp-Asp-Asp (9), (SEQ ID NO. 3)

and

Ala-Glu-Glu-Glu-Glu-Glu (10), (SEQ ID NO. 4).

In still a further aspect of the present invention, there is provided a pharmaceutical composition comprising an effective antiprotozoan, antibacterial, antiviral or antitumor amount of the above-defined physiologically active peptide or each of the above-defined physiologically active peptide compositions and at least one pharmaceutically acceptable carrier, diluent or excipient.

In each of the above amino acid sequences of formulae (1) to (10), the amino acid residue located in the left end thereof is an N-terminus amino acid residue and the amino acid residue located in the right end thereof is a C-terminus amino acid residue.

In the present invention, the activity to inhibit multiplication of Toxoplasma is evaluated by two characteristics, i.e. "percentage of cells containing Toxoplasma" and "Toxoplasma growth inhibitory factor activity (hereinafter referred to as "Toxo-GIF activity")". These characteristics are measured according to the methods described in Nagasawa, H., et.al., Jpn. J. Vet. Sci., vol. 43, pages 307–319, 1981 and Sakurai, H., et.al., Jpn. J. Trop. Med. Hyg., vol. 10, pages 183–195, 1982.

(1) Measurement of the percentage of cells containing Toxoplasma:

(a) Activities in mouse macrophages and canine monocytes:

An adult BALB/c female mouse is intraperitoneally injected with 1 ml of a sterilized saline containing 0.2% of glycogen, and, 5 days later, the peritoneal cavity of the mouse is washed with cold Hank's balanced salt solution (hereinafter referred to as "HBSS"), thereby taking up peritoneal exudate cells. These cells are washed by centrifugation at 250×G for 5 min twice, and suspended in Tc199 culture medium containing 10% of heat-inactivated calf serum (hereinafter referred to as "10%-HICS-Tc199 culture medium", see *Igaku No Ayumi* (Progress in Medicine), 62, No. 6, published on Aug. 5, 1967) in a concentration of $1\times10^6$ cells/mi. This cell suspension is portionwise poured, 1 ml each, into culture wells (Multidish-tray, FB-16-24-TC, manufactured and sold by Limblo Chemical Co., U.S.A.), which are covered by a circular cover glass having a diameter of 15 mm, and cultured in a 5% $CO_2$-incubator. In order to remove contaminating erythrocytes and lymphocytes, each of the culture wells is gently rinsed with HBSS three times at intervals of 2 hours, and then cultivated overnight in the $CO_2$-incubator to thereby form a mouse macrophage monolayer on the cover glass.

On the other hand, in the preparation of canine monocytes, 5 ml of blood is collected from cervical vein as a peripheral blood, and 0.05% of heparin is added. This blood is subjected to fractionation according to the Conray 400-Ficoll method (see Tsuji, H., *Men-eki Jikken Sosaho* (Procedure for Immunological Tests), 4th ed., Immunocells I-4, pages 443–446, published by Maeda Printing Co., Ltd., in 1979) to thereby obtain a mononuclear cell fraction. The obtained mononuclear cell fraction is subjected to centrifugation (800×G, 5 min., 4° C.) with HBSS and then with 10%-HICS-Tc199 culture medium, and suspended in 10%-HICS-Tc199 culture medium in a concentration of about $1\times10^6$ cells/mi. The resultant cell suspension is portionwise poured, 1 ml each, into the above-mentioned culture wells, which are covered by a circular cover glass having a diameter of 15 mm, and cultured in a 5% $CO_2$-incubator. The culturing is effected for 12 hours, and each of the culture wells is gently rinsed with HBSS three times, followed by cultivation overnight in the $CO_2$-incubator, to thereby form a canine monocyte monolayer on the cover glass.

Each of the above-obtained monolayers is again rinsed with 10%-HICS-Tc199 culture medium, and inoculated with $1\times10^5$ tachyzoites of Toxoplasma strain RH per $1\times10^6$ mouse macrophages or canine monocytes so that the macrophages are infected thereby. Free Toxoplasma organisms having not penetrated into the cells are removed by washing with HBSS one hour after the inoculation.

A 10%-HICS-Tc199 culture medium containing a peptide sample is applied to the cover glass in an amount of 1 ml per $1\times10^6$ cells for both of the mouse macrophages and the canine monocytes, followed by cultivation for 48 hours, and then stained with May-Grunwald-Giemsa to thereby count the number of Toxoplasma organisms in the cells. Within a certain visual field on the cover glass, 100 cells are checked to count the number of cells which contain no Toxoplasma, the number of cells which contain one to five Toxoplasm organisms and the number of cells which contain 6 or more Toxoplasma organisms, and the count results are expressed by percentage. Similar checking and counting are performed within four other visual fields on the cover glass. From the data obtained on all of the five visual fields, an average value and a standard deviation are calculated to determine the percentage of cells containing Toxoplasma.

(b) Activities in human myocardial cells (Giardi Heart cell) and human cerebral cells (Flow 3000 cell)

The cells are suspended in MEM-M culture medium containing 10% of heat-inactivated calf serum at a concentration of $1\times10^6$ cells/mi. This cell suspension is portionwise poured, 1 ml each, into culture wells (multidish-tray, FB-16-24-TC, manufactured and sold by Limblo Chemical Co., U.S.A.), which are covered by a circular cover glass having a diameter of 15 mm, and cultured in a 5% $CO_2$-incubator overnight to thereby obtain a cell monolayer (a human myocardial cell monolayer and a human cerebral cell monolayer) on the cover glass.

The obtained cell monolayer is rinsed with MEM-M culture medium, and inoculated with $1\times10^5$ tachyzoites of Toxoplasma strain RH per $1\times10^6$ cells with respect to each of the human myocardial cells and the human brain cells. Free Toxoplasma organisms having not penetrated into the cells are removed by washing with HBSS one hour after the inoculation.

An MEM-M culture medium containing a peptide sample is applied to the cover glass in an amount of 1 ml per $1\times10^6$ cells, followed by cultivation for 48 hours, and then stained with May-Grunwald-Giemsa to thereby count the number of Toxoplasma organisms in the cells. The percentage of cells containing Toxoplasma organisms is determined in the same manner as described above for mouse macrophages.

(2). Measurement of Toxo-GIF activity:

The Toxo-GIF activity, which is another activity useful for evaluating the activity to inhibit multiplication of Toxoplasma, is defined as a proportion of decrease of Toxoplasma (Tp)-containing cells (in percentage) attributed to the addition of a peptide sample, expressed by percentage, and calculated according to the following formula: Toxo-GIF Activity (%)=

$$\text{Toxo-GIF Activity (\%)} = \left(1 - \frac{\text{Percentage of Tp-containing cells in the presence of a peptide sample}}{\text{Percentage of Tp-containing cells in the absence of a peptide sample}}\right) \times 100$$

As a peptide sample, use is made of one obtained by dissolving a powdery peptide in 3 ml of 10%-HICS-Tc199 culture medium and then filtering and sterilizing the resultant solution through a membrane filter having a pore size of 0.46 μm.

In the measurements (1) and (2) above, the concentration of the sample peptide is 5.0 mg/ml for each fraction of the below-described crude Obioactin and purified Obioactin, and is 0.5 mg/ml for each of the synthetic peptides according to the present invention.

Hereinbelow, description will be made with respect to the preparation and purification of crude Obioactin fractions by high performance liquid chromatography and reverse phase chromatography, which have led to the finding of the novel physiologically active peptides of the present invention, which peptides are believed to be peptides forming active sites of Obioactin.

(I) Preparation of crude Obioactin

Among the methods of Japanese Patent Application Laid-Open Specification Nos. 57-142922 and 57-144983 and the method of Suzuki et al. (Suzuki, N. et al., Zbl. Bakt. Hyg. I. Abt. Orig., vol. A 256, pages 356–366, 1984) which are available for the preparation of crude Obioactin, the method of Suzuki et al. is chosen. According to this method, tachyzoites ($1 \times 10^8$) of Toxoplasma strain RH (available from the Obihiro University of Agriculture and Veterinary Medicine, the Department of Protozoology of the Research Institute for Microbial Diseases of Osaka University and the National Institute of Health, Japan) are intravenously injected into a normal Holstein cattle (6 to 8 months old), and 5 weeks after this initial infection, the same tachyzoites ($1\times10^8$) of Toxoplasma strain RH are injected as a booster. Two weeks after the boost, TLA (1 μg/kg body weight; prepared by the method of Igarashi, I. et.al., Zbl. Bakt. Hyg. I. Abt. Orig., vol. A 244, pages 374–382, 1979) is intravenously injected, and blood is collected 24 hours after the TLA injection. Serum is obtained from the blood, and subjected to the latex agglutination testing. Results of the testing show that the serum has an antibody titer of not lower than 1:3,200. Obioactin is prepared from the serum, as follows.

Pronase as a protease is added in an amount of 0.1 g per 100 ml of the serum, followed by incubation at 37° C. for 12 hours, and then a 10N aqueous sodium hydroxide solution is dropwise added in an amount of 10 ml per 100 ml of the serum. Alkali hydrolysis is conducted at 100° C. for an hour. The reaction mixture is cooled to 4° C., and the pH value thereof is adjusted to 7.0±0.1 by the dropwise addition of a 10N hydrochloric acid.

The resultant hydrolyzed serum is centrifuged at 10,000 rpm (10,700×G) for 20 min and residues are removed. The resultant serum is subjected to gel filtration through Sephacryl S-200 (trade name of a gel manufactured and sold by Pharmacia Fine Chemicals Co., Sweden) and then through Toyo-pearl HW-40 (trade name of a gel manufactured and sold by Tosoh Co., Japan) to obtain a fraction having Toxo-GIF activity. This fraction is lyophilized to obtain crude Obioactin.

(II) Purification of Obioactin (1) High performance liquid chromatography using DEAE-5PW column The thus obtained crude Obioactin is fractionated by DEAE-5PW column (manufactured and sold by Tosoh Co., Japan) having an inside diameter of 21.5 mm and a length of 15 cm by NaCl concentration gradient ion exchange chromatography in which a concentration gradient of NaCl from 0M to 1M is made in 0.02M ammonium acetate as a basic solution. The obtained chromatogram is shown in FIG. 1. Each of the fractions is lyophilized, desalted by gel filtration through Sephadex G-15 (trade name of a gel manufactured and sold by Pharmacia Fine Chemicals Co., Sweden) and lyophilized again. An aliquot of the resultant powder from each of the fractions is dissolved in 10%-HICS-Tc199 culture medium in a concentration of 5 mg/ml, and the Toxo-GIF activity thereof is measured using mouse peritoneal macrophages. Results are shown in Table 1.

TABLE 1

| | Activities of DEAE-5PW fractions to inhibit multiplication of Toxoplasma | | | | |
|---|---|---|---|---|---|
| | Percentage* of cells containing Toxoplasma (Tp) (%) | | | Toxo-GIF activity | Cyto- |
| Sample | 0 Tp | 1–5 Tp | ≧6 Tp/cell | (%) | toxicity |
| Control (Tc-199) | 62.8 ± 7.5 | 22.6 ± 4.9 | 14.6 ± 3.9 | — | — |
| Fraction 1 | 48.6 ± 9.3 | 29.0 ± 3.8 | 22.4 ± 8.8 | −38.2 | — |
| Fraction 2 | 66.8 ± 15.7 | 17.8 ± 8.6 | 15.4 ± 8.8 | 10.8 | — |
| Fraction 3 | 71.4 ± 11.4 | 17.8 ± 4.8 | 10.8 ± 7.4 | 23.1 | — |
| Fraction 4 | 68.8 ± 10.8 | 17.4 ± 5.9 | 13.6 ± 5.6 | 16.1 | — |

(*: average ± standard deviation)

As shown in Table 1, the Toxo-GIF activity is −38.2% for the first fraction, 10.8% for the second fraction, 23.1% for the third fraction and 16.1% for the fourth fraction. In view of these results, the third fraction is collected as the most active fraction, and purified according to the following purification procedure.

(2) ODS-120T reverse phase chromatography

Figure 2:
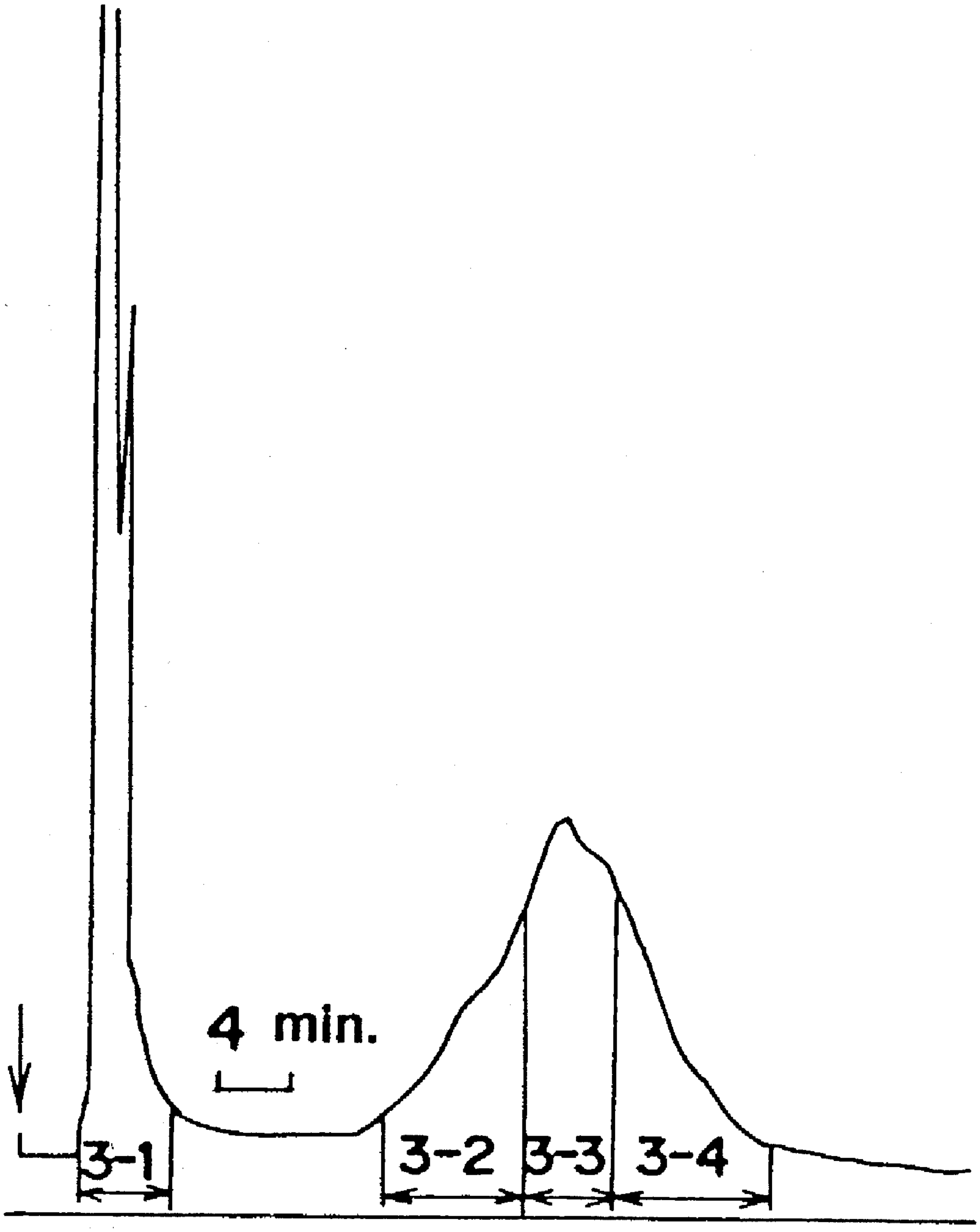
FIG. 2 shows a chromatogram obtained by reverse phase chromatography of the 3rd fraction as indicated in FIG. 1.

The above-obtained third fraction is subjected to reverse phase chromatography using ODS-120T column (manufactured and sold by Tosoh Co., Japan) with a concentration gradient of 10% to 100% of acetonitrile in 0.1% trifluoroacetic acid solution, to thereby obtain a chromatogram as shown in FIG. 2. The Toxo-GIF activity of each of the fractions is measured, and results are shown in Table 2.

TABLE 2

Activities of ODS-120T fractions to inhibit multiplication of Toxoplasma

| Sample | Percentage* of cells containing Toxoplasma (Tp) (%) 0 Tp | 1–5 Tp | ≧6 Tp/cell | Toxo-GIF activity (%) | Cyto-toxicity |
|---|---|---|---|---|---|
| Control (Tc-199) | 49.8 ± 16.3 | 25.8 ± 7.1 | 23.4 ± 9.3 | — | — |
| Fraction 3-1 | 98.8 ± 1.1 | 1.2 ± 1.1 | 0 | 97.6 | — |
| Fraction 3-2 | 98.4 ± 1.5 | 1.6 ± 1.5 | 0 | 96.8 | — |
| Fraction 3-3 | 98.6 ± 2.1 | 1.2 ± 1.6 | 0 | 97.3 | — |
| Fraction 3-4 | 99.6 ± 0.5 | 0.4 ± 0.5 | 0 | 99.2 | — |

(*: average ± standard deviation)

As shown in Table 2, the Toxo-GIF activity is 97.6% for Fraction 3-1, 96.8% for Fraction 3-2, 97.3% for Fraction 3-3 and 99.2% for Fraction 3-4.

As mentioned hereinbefore, the present inventor previously investigated the amino acid sequence of Fraction 3-4, and developed a physiologically active peptide (see U.S. Pat. No. 4,897,463).

In the subsequent investigation toward the present invention, the present inventor has analyzed the amino acid sequence of Fraction 3-3.

(III) Analysis of amino acid sequence of Fraction 3-3

The purified Obioactin fraction [ODS-120T Fraction 3-3, 800 pmol] is put, together with 0.2 ml of a constant boiling point hydrochloric acid solution (6N) containing 0.1% of thioglycol, into a tube, and the tube is sealed. The contents of the tube are heated at 110° C. for 24 hours to thereby hydrolyze the Obioactin fraction. The amino acid composition of the resultant hydrolyzate is analyzed by the OPA method (see Benson, R. J., et al., Proc. Nat. Acad. Sci., USA., vol. 72, pages 619–622, 1975; and Bohlen, P., Method in Enzymology, vol. 91. pages 17–26, 1984) using Hitachi Model 83 Amid Acid Analyzer.

The amino acid sequence is analysed in accordance with the Edman degradation method using Protein Sequencer (manufactured and sold by Applied Biosystems, U.S.A.). The collected Edman cycles are converted to derivatives of 3-phenyl-2-thiohydantoin (PTH), and PTH-amino acids are identified by reverse phase high pressure liquid chromatography. Results are shown in Table 3.

TABLE 3

Amino acid composition (unit: pmol) of purified Obioactin (800 pmol) (ODS-120T Fraction 3-3)

| Amino acid No. | Ala | Val | Glu | Gly | Pro | Tyr |
|---|---|---|---|---|---|---|
| 1 | 140 | 55 | 62 | 94 | 100 | — |
| 2 | 70 | 112 | 100 | — | — | — |
| 3 | — | 103 | 100 | — | — | — |
| 4 | — | — | — | — | 101 | — |
| 5 | — | 100 | — | — | — | |
| 6 | — | 112 | — | — | — | — |
| 7 | — | — | — | — | 10 | 51 |

(the figures below the first place of decimals have been omitted)

As shown in Table 3 above, with respect to Fraction 3-3, the amino acids which are found as the first amino acid residue, as counted from the N-terminus thereof, of the amino acid sequence, include alanine (Ala, 140 pmol), valine (Val, 55 pmol), glutamic acid (Glu, 62 pmol), glycine (Gly, 90 pmol) and proline (Pro, 100 pmol); those which are found as the second amino acid residue include Val (112 pmol), Glu (100 pmol) and Ala (70 pmol); those which are found as the third amino acid residue include Val (103 pmol) and Glu (100 pmol); those which are found as the fourth, the fifth and the sixth amino acid residues include Pro (101 pmol), Val (100 pmol), and Val (112 pmol), respectively; and those which are found as the seventh amino acid residue include tyrosine (Tyr, 51 pmol) and Pro (10 pmol).

The above results strongly suggest that this purified Obioactin is composed of a mixture of at least five peptides which have, respectively, Ala, Pro, Gly, Glu and Val as the first amino acid residue. The results also suggest that the other amino acid residues of these peptides are chains of amino acid residues selected from Glu, Val, Ala and Pro.

Further, the above-obtained purified Obioactin Fraction 3-3 cannot be purified anymore despite repeated treatments by chromatography. The reason for this is believed to be that Fraction 3-3 is a mixture of similar peptides which have heterologous N-terminals.

From the above results, it is only deduced that the peptides constituting Fraction 3-3 of purified Obioactin have Ala, Pro, Gly or Glu at the N-terminus thereof and 2 to 6 molecules selected from Glu, Ala, Pro and Val as the subsequent amino acid residues. Therefore, the amino acid sequences for the peptides forming the active sites of Fraction 3-3 of Obioactin cannot be directly determined.

In this situation, the present inventor has synthesized an extremely large number of peptides corresponding to the possible amino acid sequences for Fraction 3-3 of Obioactin, and has evaluated the activity of these peptides to inhibit the multiplication of Toxoplasma. As a result, the present inventor has successfully developed a substantially pure, physiologically active peptide comprising an amino acid sequence selected from the group consisting of amino acid sequences represented by the following formulae (2) to (6):

Pro-Val-Val (2),

Glu-Pro-Val-Val (3), (SEQ ID NO. 7)

Glu-Glu-Pro-Val-Val (4), (SEQ ID NO. 8)

Ala-Glu-Glu-Pro-Val-Val (5), (SEQ ID NO. 9)

and

Gly-Ala-Glu-Glu-Pro-Val-Val (6), (SEQ ID NO. 10).

On the other hand, the present inventor has made a further study on Fraction 3-4 shown in FIG. 2 in order to develop a new peptide having the activity to inhibit the multiplication of Toxoplasma and having a more simple amino acid structure. As a result, it has unexpectedly been found that a peptide having an amino acid sequence composed of only two amino acids, i.e., Gly and Glu, exhibits immunoregulatory activities comparable to those of the above peptides of formulae (2)–(6). This new peptide has an amino acid sequence represented by the formula Gly-Glu (1) (SEQ ID NO. 5).

The present inventor has also found that, among the peptides respectively comprised of the amino acid sequences of formulae (1) to (6), the peptides comprising the amino acid sequences of formulae (5), (6) and (1) exhibit higher Toxo-GIF activities than the other peptides. The present inventor has designated the peptides comprising the amino acid sequences of formulae (5), (6) and (1) as "Obio-2", "Obio-3"and "Obio-4", respectively.

Surprisingly, the present inventor has also found that a physiologically active peptide composition comprising at least two peptides selected from the peptides comprising amino acid sequences represented by formulae (1) to (6) and a physiologically active peptide composition comprising at least one peptide selected from these peptides (1) to (6) and at least one additional peptide selected from the peptides disclosed in U.S. Pat. No. 4,897,463, i.e., peptides comprising amino acid sequences represented by formulae (7) to (10) described above, exhibit synergistically improved, extremely high Toxo-GIF activities.

With respect to the above-mentioned physiologically active peptide compositions, the proportions of the individual component peptides are not particularly limited, but can be varied depending on the objective of use and the desired effect. In general, however, it is preferred that the individual component peptides be used in equal amounts or amounts which are not smaller than half of the amount corresponding to the equal amount.

The physiologically active peptide of the present invention can be produced by the conventional method for peptide synthesis (see, for example, Kent, S. B., et al. "Peptides 1984", page 185, edited by U. Ragnarsen, and published by Almqvist and Wiksell, Stockholm, Sweden, 1984).

Further, if desired, the physiologically active peptide of the present invention can also be produced by a recombinant DNA technique, utilizing a DNA coding for each peptide in combination with an appropriate host vector system.

In these manners, the physiologically active peptide of the present invention can be obtained in a substantially pure form.

As mentioned above, the physiologically active peptide of the present invention not only has immunoregulatory activities, that is, activities to inhibit the multiplication of various types of microorganisms, such as protozoa, bacteria and viruses and to suppress tumors, but also exhibits low toxicity, so that the present peptide is useful as an active ingredient of a pharmaceutical composition for humans and other mammals. In this connection, it is noted that the experiment shows that the survival periods of tumor-bearing mice can be prolonged when the mice are administrated with the physiologically active peptide of the present invention in combination with a conventional antitumor drug, for example, Futraful (FT207) (manufactured and sold by Taiho Pharmaceutical Co., Ltd., Japan).

When the physiologically active peptide of the present invention is used for the treatment of human and animal patients, the physiologically active peptide of the present invention may be used in the form of a pharmaceutical composition comprising an effective antiprotozoan, antibacterial, antiviral or antitumor amount of the physiologically active peptide and at least one pharmaceutically acceptable carrier, diluent or excipient. If desired, this pharmaceutical composition may contain customary additives, such as, a stabilizer, a solubilizer, a buffer, a soothing agent, a preservative and a colorant. Further, other medicines may optionally be incorporated into the peptide of the present invention.

The peptide of the present invention may preferably be employed in the form of an injection (e.g., a liquid preparation, a suspension and an emulsion), but the form in which the peptide is used is not limited to an injection. As an injection, the pharmaceutical composition of the present invention may be administered in a usual manner. That is, the injection may be intravenously administered alone or in combination with a liquid which is usually employed as a replenisher, such as glucose, an amino acid and the like. If desired, the injection may be administered intramuscularly, hypodermically, intradermically or intraperitoneally. Furthermore, the peptide of the present invention may be in a form other than an injection, for example, a form suitable for oral administration.

The amount of the physiologically active peptide to be used in the pharmaceutical composition of the present invention and the dose of the pharmaceutical composition of the present invention may be appropriately chosen according to the manner of administration, the dosage form, the objective of use, the conditions of the patient and the like. For example, in the case of an injection containing about 1 to 80% by weight of the active ingredient, it is generally preferred that the injection be administered so that the amount of the active ingredient given to the patient is in the range of from about 0.001 to 10 mg/kilogram/day. The daily dose is not necessarily administered at one time, and may be administered portionwise in 3 to 4 doses of administration. In the case of a dosage form other than an injection, the dose may be appropriately selected, using as a criterion the above-mentioned general description about the dose of the injection.

DETAILED DESCRIPTION OF THE PREFERRED EMBODIMENTS

The present invention now will be described in more detail with reference to the following Examples, Referential Example and Application Example, which should not be construed as limiting the scope of the present invention.

EXAMPLE 1

(Synthesis of peptide comprising an amino acid sequence represented by formula (5) (Ala-Glu-Glu-Pro-Val-Val) and purification thereof)

(1) Solid phase synthesis of peptide by t-Boc (tert-butoxycarbonyl group) method The following apparatus and reagents are used.

Apparatus: peptide synthesizer apparatus, Model 9600 (manufactured and sold by Milligen/Biosearch Co., Ltd., U.S.A.)

Reagents: When the amino acid sequence is input into the apparatus and a simulation of the synthesis of the peptide is conducted, the apparatus provides instructions about the types and amounts of the necessary reagents.

Resin:
- Boc-Val-resin

Amino acid:
- Boc-Ala
- Boc-Glu (OBzl)
- Boc-Pro
- Boc-Val

Auxiliary reagent:
- DCM (dichloromethane)
- DMF (dimethylformamide)
- DCM/DMF=1/1

Capping reagent:
- I-acetylimidazole in DMF

Basewash:
- DIPEA (Diisopropylethylamine) in DCM deblocking reagent
- 45.0% TFA (trifluoroacetic acid)
- 2.5% anisole
- 52.5% DCM Activator:
- DIPCDI (diisopropylcarbodiimide) in DCM The necessary reagents as mentioned above (all of which are reagents for peptide synthesis manufactured by Watanabe Chemical Co., Ltd., Japan) are put in the bottles connected to the apparatus, and then the synthesis is started.

(Method of synthesis)

The synthesis proceeds from the C-terminus to the N-terminus. The protective group of the N-terminus of Boc-Val-resin (the amino acid for forming the C-terminus of the sequence), which has been put in the reaction vessel, is subjected to deblocking to remove the protective group. Then, the resultant resin is subjected to stirring by means of argon gas, together with an amino acid (Boc-Val) for the second amino acid residue which has been sufficiently activated by an activator, thereby effecting coupling. The coupling reaction is allowed to proceed until the bonding between the first and second amino acid residues on the side of the C-terminus becomes satisfactory (the time necessary for this procedure can be calculated by the above-mentioned synthesis simulation). Then, the protective group of the amino acid for the second amino acid residue is subjected to deblocking.

Then, the portion of the first amino acid residue having failed to undergo the coupling (that is, the first amino acid residue having no second residue bonded thereto) is subjected to capping reaction. Due to this capping reaction, this portion remaining unbonded to the second amino acid residue can be prevented from participating in the subsequent synthesis reaction so that the final synthetic peptide advantageously contains no undesired peptide product in which one or more residues are missing.

Thereafter, substantially the same procedure as mentioned above, i.e., deblocking, activation, coupling and capping are automatically repeated to thereby obtain the desired synthetic peptide.

(2) Separation of synthetic peptide from solid phase (resin)

At the time of the completion of the synthesis the C-terminus of the peptide chain is attached to the resin. In addition, the peptide chain has a protective group at its side chain. Therefore, in order to render the peptide suitable for utilization, it is necessary that the synthetic peptide be separated from the resin and the protective group attached to the side chain thereof be removed to deblock the side chain.

In the case of the t-Boc method, HF (hydrogen fluoride) is generally employed for the separation and deblocking operations. Illustratively stated, an equal amount of anisole is added to the produced synthetic peptide (which is bonded to the resin), and the resultant mixture is reacted at 0° C. in HF for one hour using a separation apparatus. As a result, the synthetic peptide is separated from the resin.

(3) Extraction of peptide

After completion of the separation, HF is removed, TFA is added, and the resultant mixture is filtered through a glass filter (3G3) into a flask containing cooled ether. The resin is left on the filter upon the filtration.

White precipitate produced in the ether is separated by centrifugation, and the supernatant is discarded. Cooled ether is further added to the separated precipitate, followed by agitation, and then subjected to centrifugation. These are repeated two or three times to thereby remove nonpolar impurities mixed with the peptide, and the resultant precipitate is collected and dried.

(4) Purification by chromatography

The thus separated and deblocked crude peptide is analyzed and fractionated employing the following column, eluent and conditions:

Column ODS
  reverse phase column (TSKgel ODS-BOTm, Tosoh Co., Japan)
  for analysis 4.8×15 cm
  for fractionation 21.5×30 cm
Eluent A:
  pure water containing 0.1% TFA
  B: acetonitril containing 0.1% TFA
  A:B=95.5-30:70 linear gradient
  at analysis 30 minutes
  at fractionation 90-120 minutes
Detection by UV 230 nm.

The desired peptide can be confirmed as a clear main peak (rough retention time can be estimated by considering the type of constituent amino acids, that is, the hydrophobic properties thereof, the degree of ionization in 0.1% TFA (about pH 2.0) and the like). It is recommended, however, to retain fractions of other peaks as well for certainty. When any single main peak cannot be identified for some reason, reanalysis, such as by amino acid analysis, protein sequencer analysis or manual Edman degradation, is conducted with respect to the purified peptide.

The synthetic peptide of formula (5) is obtained and the amino acid sequence thereof confirmed, as described above.

EXAMPLE 2–5

Each of the peptides represented by formulae (1), (2), (3), (4) and (6) is individually synthesized in substantially the same manner as in Example 1 except that amino acid raw materials are changed to those corresponding to the peptide, and the amino acid structure thereof is confirmed.

Referential Example 1

Obio-1 peptide is synthesized in substantially the same manner as in Example 1 except that amino acid raw materials are changed to those corresponding to the peptide Obio-1 represented by formula (7), and the amino acid structure thereof is confirmed.

Application Example

The activities of the physiologically active peptides of the present invention (hereinafter frequently referred to as "synthetic peptides") are evaluated.

(A) Toxo-GIF activity in mouse macrophage

The synthetic peptides are individually dissolved in a culture medium in such an amount that the concentration becomes 0.7 mM, and the Toxo-GIF activities of the peptides are determined, using mouse peritoneal macrophages. The results are shown in Table 4.

TABLE 4

| | | | | Activity of synthetic peptides to inhibit multiplication of Toxoplasma | | | | | |
|---|---|---|---|---|---|---|---|---|---|
| | | | | Percentage of cells containing Toxoplasma (Tp) (%) | | | Toxo-GIF | | |
| Sample | M.W. | mM | mg/ml | 0 Tp | 1–5 Tp | ≧6 Tp/cell | (%) | Cytotoxicity | Memo |
| A. 10%-HICS-Tc199 (Negative control) | — | — | — | 7.2 ± 4.4 | 21.8 ± 4.6 | 71.0 ± 4.5 | — | — | |
| B. GEEEEE | 720 | 0.7 | 0.50 | 66.6 ± 15.3 | 31.8 ± 14.0 | 1.6 ± 1.9 | 64.0 | — | Obio-1 |

TABLE 4-continued

Activity of synthetic peptides to inhibit multiplication of Toxoplasma

| Sample | M.W. | mM | mg/ml | Percentage of cells containing Toxoplasma (Tp) (%) 0 Tp | 1–5 Tp | ≧6 Tp/cell | Toxo-GIF (%) | Cytotoxicity | Memo |
|---|---|---|---|---|---|---|---|---|---|
| Known peptide) (Positive control) | | | | | | | | | |
| C. Native Obioactin | <5000 | — | 5 | 53.5 ± 7.3 | 38.4 ± 6.2 | 8.1 ± 5.3 | 49.9 | — | |
| D. Synthetic peptide | | | | | | | | | |
| 1. GE | 204 | 0.7 | 0.14 | 51.7 ± 5.9 | 41.6 ± 7.7 | 7.8 ± 3.4 | 47.6 | — | Obio-4 |
| 2. PVV | 313 | 0.7 | 0.22 | 35.2 ± 14.1 | 33.0 ± 10.2 | 31.8 ± 7.3 | 30.2 | — | |
| 3. EPVV | 442 | 0.7 | 0.31 | 32.6 ± 14.0 | 51.0 ± 7.5 | 16.4 ± 8.4 | 27.4 | — | |
| 4. EEPVV | 571 | 0.7 | 0.40 | 35.2 ± 11.5 | 38.0 ± 10.6 | 26.8 ± 11.0 | 30.2 | — | |
| 5. AEEPVV | 642 | 0.7 | 0.45 | 64.4 ± 9.3 | 32.8 ± 8.8 | 2.8 ± 1.1 | 61.6 | — | Obio-2 |
| 6. GAEEPVV | 699 | 0.7 | 0.49 | 55.2 ± 6.2 | 36.2 ± 8.6 | 8.6 ± 4.4 | 51.7 | — | Obio-3 |

The abbreviations for amino acids are as follows:
E: Glu, G: Gly, A: Ala, D: Asp, P: Pro and V: Val.

As shown in Table 4, the Toxo-GIF activities of the synthetic peptides are 47.6% for peptide No. 1 (Obio-4), 30.2% for peptide No. 2, 27.4% for peptide No. 3, 30.2% for peptide No. 4, 61.6% for peptide No. 5 (Obio-2)and 51.7% for peptide No. 6 (Obio-3). All of the tested peptides exhibit no cytotoxicity at the above-mentioned concentration (0.7 mM) used in the test.

Peptide No. 1 (Obio-4), peptide No. 5 (Obio-2) and peptide No. 6 (Obio-3) exhibit high activities. The molecular weights of peptides Nos. 5 (Obio-2) and 6 (Obio-3) are about 642 and about 699, respectively. Further, each of synthetic peptides Nos. 2, 3 and 4 can also be utilized as a drug having the ability to inhibit the multiplication of Toxoplasma and to activate the immune system.

The Toxo-GIF activity of crude Obioactin becomes appreciable at a concentration as high as about 5 mg/ml. By contrast, sufficient Toxo-GIF activity of the synthetic peptide of the present invention, e.g., peptide No. 5 (Obio-2), is detected even at a concentration as low as 0.25 mg/ml. From the above, it is estimated that the activity of the synthetic peptide of the present invention is 10 to 20 times that of crude Obioactin on a weight basis, and 40 to 140 times that of crude Obioactin on a mole basis.

(B) Toxo-GIF activities in mouse macrophage, canine monocyte, human myocardial cell and human cerebral cell The effect of the No. 5 peptide (Obio-2) is evaluated. As shown in Table 5, significant Toxo-GIF activities are observed in each of the cells, and thus, it is confirmed that the synthetic peptide of the present invention does not show species specificity as in the case of crude Obioactin.

TABLE 5

Activity of synthetic peptide No. 5 (Ala—Glu—Glu—Pro—Val—Val; Obio-2) to inhibit multiplication of Toxoplasma in mouse, canine and human cells

| Cell | Obio-2 concentration (mg/ml) | Percentage of cells containing Toxoplasma (Tp) (%) 0 Tp | 1–5 Tp | ≧6 Tp/cell | Toxo-GIF (%) | Cytotoxicity |
|---|---|---|---|---|---|---|
| Mouse macrophage | 0 | 76.6 ± 9.2 | 16.5 ± 5.1 | 7.2 ± 4.3 | — | — |
| | 0.05 | 88.4 ± 7.6 | 7.0 ± 4.5 | 4.6 ± 4.2 | 50.4 | — |
| Canine monocyte cell | 0 | 40.1 ± 15.5 | 28.5 ± 6.5 | 31.3 ± 8.2 | — | — |
| | 0.05 | 80.5 ± 6.4 | 12.8 ± 5.4 | 6.7 ± 3.3 | 67.4 | — |
| Human myocardial cell | 0 | 54.4 ± 18.3 | 23.5 ± 9.3 | 22.1 ± 9.7 | — | — |
| | 0.05 | 80.7 ± 6.1 | 10.6 ± 3.4 | 8.7 ± 2.1 | 57.7 | — |
| Human cerebral cell | 0 | 32.6 ± 14.0 | 51.1 ± 7.5 | 16.4 ± 8.4 | — | — |
| | 0.05 | 75.4 ± 7.4 | 12.6 ± 6.8 | 2.1 ± 1.9 | 78.2 | |

(C) Effect of the injection of novel synthetic peptides on a Methylcholanthrene induced tumor (MC tumor )-bearing mouse Methylcholanthrene induced tumor cells excised from an MC induced tumor lump of a BALB/c mouse having, injected thereto, 0.5 mg of 20-Methylcholanthrene (manufactured and sold by Wako Pure Chemical Industries Ltd.), are suspended in RPMI-1640 culture medium, thereby obtaining a cell suspension of $2\times10^7$ cells/ml. 0.025 ml ($5\times10^5$ MC tumor cells/mouse) of the cell suspension is intramuscularly injected under the skin on the back of a 6-week-old male mouse to inoculate the mouse with MC-tumor cells, thereby obtaining a tumor-bearing mouse.

Each of Obio-2 and Obio-3 is intramuscularly injected in an amount of 30 μg/mouse under the skin on the back of the mouse every week after the injection of the above MC tumor cell suspension to evaluate the inhibitory effect thereof on the multiplication of the tumor. Five tumor-bearing mice are employed for each test, and an average is taken. Results, together with the control data on Obio-uninjected mice, are shown in FIG. 3.

Figure 3:
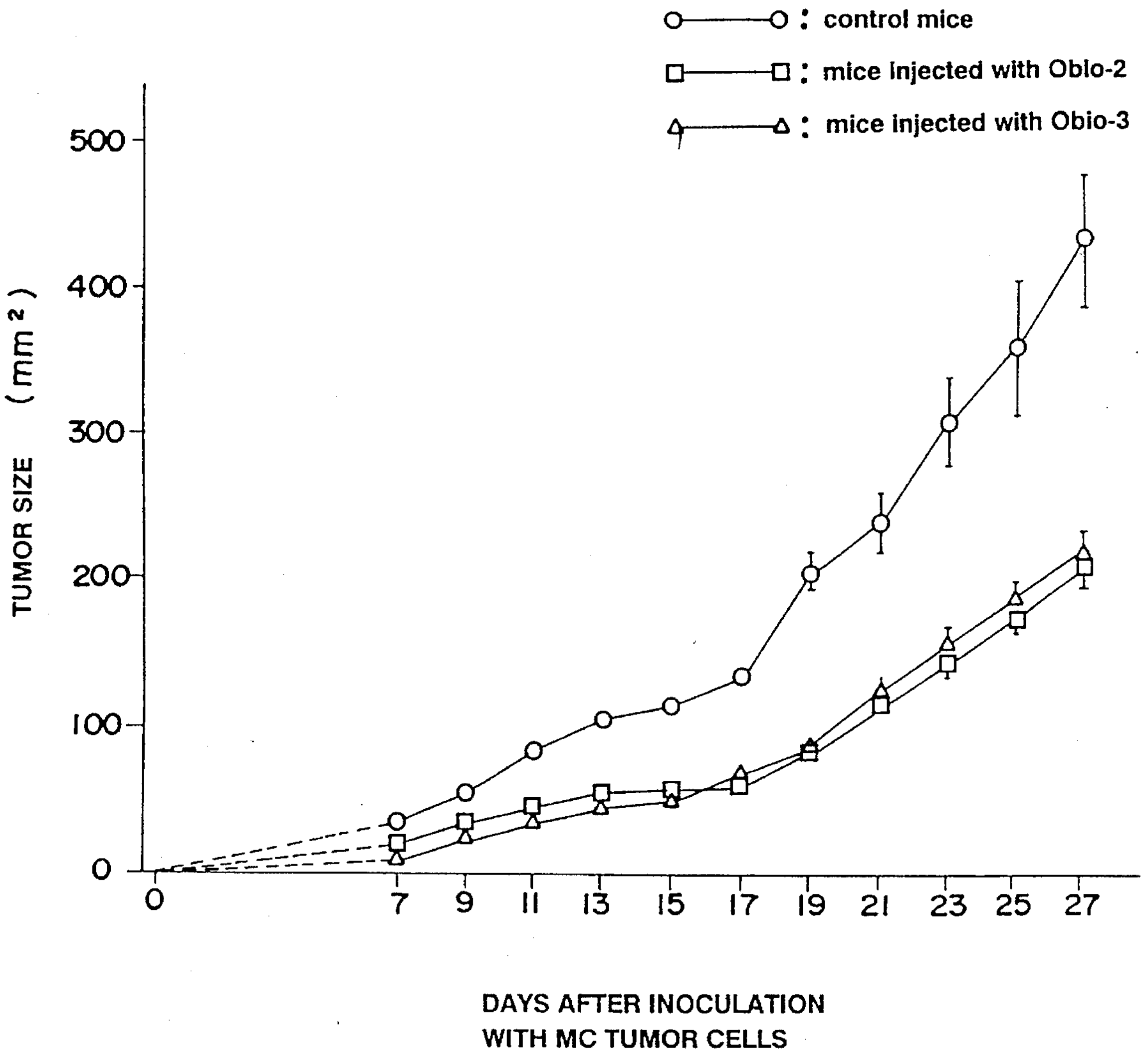
FIG. 3 is a graph showing the effect of the physiologically active peptide according to the present invention on the multiplication of tumor cells in mice.

As shown in FIG. 3, the average tumor area measured 28 days after the inoculation with tumor cells is 432±10.5 $mm^2$ for the first group (control) in which physiological saline as control is injected, 208±40.1 $mm^2$ for the second group in which Obio-2 is injected, and 219±40.1 $mm^2$ for the third group in which Obio-3 is injected. These demonstrate that the multiplication of tumors is remarkably inhibited in the groups injected with Obio-2 and Obio-3 as compared to the control group not injected with them.

(D) Synergistic effect of the use of peptides in combination

A study is made regarding the synergistic effect of the use of synthetic peptides Obio-2 and Obio-3 having exhibited high Toxo-GIF activities in combination and the use of each thereof in combination with peptide Obio-1. As shown in Table 6, the Toxo-GIF activity is synergistically increased by the use of the peptides in combination.

TABLE 6

Increase in Toxo-GIF activity by the use of individual synthetic peptides (Obio-2 and 3) in combination and the use of each thereof in combination with peptide (Obio-1)

| Sample | (mg/ml) | Percentage of cells containing Toxoplasma (Tp) (%) 0 Tp | 1–5 Tp | ≧6 Tp/cell | Toxo-GIF (%) | Cyto-toxi-city |
|---|---|---|---|---|---|---|
| 10% HICS-Tc199 (control) | | 17.6 ± 8.6 | 28.0 ± 4.4 | 54.4 ± 9.1 | — | — |
| Native Obioaction (control) | 5.00 | 35.8 ± 20.1 | 34.1 ± 8.1 | 29.6 ± 15.6 | 22.1 | — |
| Obio-1 (known peptide) | 0.49 | 48.8 ± 15.0 | 33.8 ± 9.7 | 17.4 ± 8.7 | 37.9 | — |
| Obio-2 | 0.50 | 69.6 ± 11.5 | 24.0 ± 9.1 | 6.4 ± 2.7 | 63.1 | — |
| Obio-3 | 0.45 | 59.7 ± 15.8 | 29.5 ± 11.0 | 10.8 ± 7.1 | 51.1 | — |
| Obio-1 (0.24 mg/ml) + Obio-2 (0.25 mg/ml) | 0.49 | 85.2 ± 6.6 | 12.2 ± 5.8 | 2.6 ± 2.3 | 82.0 | — |
| Obio-1 (0.24 mg/ml) + Obio-3 (0.22 mg/ml) | 0.46 | 81.8 ± 3.3 | 14.4 ± 2.6 | 3.6 ± 1.3 | 77.9 | — |
| Obio-2 (0.25 mg/ml) + Obio-3 (0.22 mg/ml) | 0.47 | 72.4 ± 9.9 | 19.4 ± 11.8 | 6.2 ± 4.1 | 66.5 | — |

(E) Variation of the number of mononuclear cells in spleen of MC tumor-bearing mouse As shown in Table 7 below, the number of mononuclear cells in the spleen of control tumor-bearing mice injected with none of Obio-2 and Obio-3 is decreased to as small a number as 10% that of normal mice. On the other hand, the number of mononuclear cells in the spleen of tumor-bearing mice injected with Obio-2 and Obio-3 experience only a slight decrease, and retains as large a number as 65 to 70% of that of normal mice. In the histopathological findings of these spleens, no significant change is observed in the spleen follicles of both the tumor-bearing mouse groups injected with Obio-2 and Obio-3 and the tumor-bearing mouse group injected with none of them. However, in the mouse groups injected with Obio-2 and Obio-3, small mononuclear cells (small lymphocytes) and large monocytes in the spleen red marrow conspicuously gather in the mallow, especially around the vessels, whereas the control mouse group not injected with the peptide has only small lymphocytes in the marrow. Further, large bleeding colonies are clearly observed at the tumor tissue portions of the mice not injected with any of Obio-2 and Obio-3, whereas no apparent bleeding colonies are observed in the mice injected with Obio-2 and Obio-3.

The above injection of an extremely small amount (30 μg once a week) of each of synthetic peptides Obio-2 and Obio-3 into tumor-bearing mice shows that these synthetic peptides are substances which strongly act in vivo on the mononuclear cells in the spleen, especially on the large circular cells (monocyte-macrophage).

TABLE 7

Effect of the injection of synthetic peptides on the number of mononuclear cells of spleen in MC tumor-bearing mouse

| Organ | Mouse | Number of mononuclear cells per mouse | Ratio of tumor-bearing cells to normal cells |
|---|---|---|---|
| Spleen | Normal mouse | $13.0 \times 10^7$ | 1.00 |
| | Tumor-bearing mouse | | |
| | 1. Injection of physiological saline | $1.3 \times 10^7$ | 0.10 |
| | 2. Injection of Obio-2 | $8.3 \times 10^7$ | 0.64 |
| | 3. Injection of obio-3 | $9.1 \times 10^7$ | 0.72 |

What is claimed is:

1. A substantially pure, physiologically active peptide consisting of an amino acid sequence represented by a formula selected from the group consisting of formulae (3) to (6):

Glu-Pro-Val-Val (3),

Glu-Glu-Pro-Val-Val (4),

Ala-Glu-Glu-Pro-Val-Val (5), and

Gly-Ala-Glu-Glu-Pro-Val-Val (6).

2. A physiologically active peptide composition consisting essentially of at least two peptides selected from the group consisting of substantially pure, physiologically active peptides respectively consisting of amino acid sequences of formulae (1) to (6):

Gly-Glu (1),

Pro-Val -Val (2),

Glu- Pro-Val -Val (3),

Glu-Glu-Pro-Val-Val (4),

Ala-Glu-Glu-Pro-Val-Val (5), and

Gly-Ala-Glu-Glu-Pro-Val-Val (6).

3. A physiologically active peptide composition consisting essentially of at least one peptide selected from the group consisting of substantially pure, physiologically active peptides respectively consisting of amino acid sequences of formulae (1) to (6):

Gly-Glu (1),

Pro-Val-Val (2),

Glu-Pro-Val-Val (3),

Glu-Glu-Pro-Val-Val (4),

Ala-Glu-Glu-Pro-Val-Val (5), and

Gly-Ala-Glu-Glu-Pro-Val-Val (6);

and at least one peptide selected from the group consisting of substantially pure, physiologically active peptides respectively consisting of amino acid sequences of formulae (7) to (10):

Gly-Glu-Glu-Glu-Glu-Glu (7),

Glu-Glu-Glu-Glu-Glu (8),

Asp-Asp-Asp-Asp-Asp (9), and

Ala-Glu-Glu-Glu-Glu-Glu (10).

* * * * *

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
( A ) LENGTH: 6 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:1:

```
Gly Glu Glu Glu Glu Glu
1               5
```

( 2 ) INFORMATION FOR SEQ ID NO:2:

( i ) SEQUENCE CHARACTERISTICS:
( A ) LENGTH: 5 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:2:

```
Glu Glu Glu Glu Glu
1               5
```

( 2 ) INFORMATION FOR SEQ ID NO:3:

( i ) SEQUENCE CHARACTERISTICS:
( A ) LENGTH: 5 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:2:

```
Asp Asp Asp Asp Asp
1               5
```

( 2 ) INFORMATION FOR SEQ ID NO:4:

( i ) SEQUENCE CHARACTERISTICS:
( A ) LENGTH: 6 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:4:

```
Ala Glu Glu Glu Glu Glu
1               5
```

( 2 ) INFORMATION FOR SEQ ID NO:5:

( i ) SEQUENCE CHARACTERISTICS:
( A ) LENGTH: 2 amino acids
( B ) TYPE: amino acid
( C ) STRANDEDNESS: single
( D ) TOPOLOGY: linear -continued ( i i ) MOLECULE TYPE: peptide ( x i ) SEQUENCE DESCRIPTION: SEQ ID NO:5:

Gly Glu
1

( 2 ) INFORMATION FOR SEQ ID NO:6:

( i ) SEQUENCE CHARACTERISTICS:
( A ) LENGTH: 3 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:6:

Pro Val Val
1

( 2 ) INFORMATION FOR SEQ ID NO:7:

( i ) SEQUENCE CHARACTERISTICS:
( A ) LENGTH: 4 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:7:

Glu Pro Val Val
1

( 2 ) INFORMATION FOR SEQ ID NO:8:

( i ) SEQUENCE CHARACTERISTICS:
( A ) LENGTH: 5 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:8:

Glu Glu Pro Val Val
1 5

( 2 ) INFORMATION FOR SEQ ID NO:9:

( i ) SEQUENCE CHARACTERISTICS:
( A ) LENGTH: 6 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:9:

Ala Glu Glu Pro Val Val
1 5

( 2 ) INFORMATION FOR SEQ ID NO:10:

( i ) SEQUENCE CHARACTERISTICS:
( A ) LENGTH: 7 amino acids
( B ) TYPE: amino acid
( C ) STRANDEDNESS: single -continued ( D ) TOPOLOGY: linear ( i i ) MOLECULE TYPE: peptide ( x i ) SEQUENCE DESCRIPTION: SEQ ID NO:10:

```
Gly Ala Glu Glu Pro Val Val
1               5
```